US007126028B1

(12) United States Patent
O'Hagan

(10) Patent No.: US 7,126,028 B1
(45) Date of Patent: Oct. 24, 2006

(54) PROCESS FOR PREPARING CHIRAL COMPOUNDS

(75) Inventor: David O'Hagan, Durham (GB)

(73) Assignee: The University Court of the University of St. Andrews, Fife (GB)

( * ) Notice: Subject to any disclaimer, the term of this patent is extended or adjusted under 35 U.S.C. 154(b) by 0 days.

(21) Appl. No.: 09/857,465

(22) PCT Filed: Dec. 6, 1999

(86) PCT No.: PCT/GB99/04031

§ 371 (c)(1),
(2), (4) Date: Jun. 5, 2001

(87) PCT Pub. No.: WO00/34210

PCT Pub. Date: Jun. 15, 2000

(30) Foreign Application Priority Data

Dec. 5, 1998 (GB) ................................. 9826700.8

(51) Int. Cl.
*C07C 211/03* (2006.01)
*C07D 263/04* (2006.01)
*C07D 207/08* (2006.01)

(52) U.S. Cl. ....................... 564/316; 564/317; 548/230; 548/566

(58) Field of Classification Search ................ 564/424, 564/425, 510
See application file for complete search history.

(56) References Cited

FOREIGN PATENT DOCUMENTS

DE 25 38 424 3/1977
JP 9 143173 6/1997

OTHER PUBLICATIONS

Sigma Chemical Company catalog, 1992, p. 195.*
Database CAPLUS on STN, Acc. No. 1964:41463, Hano et al., Arch. Immunol. Terapii Doswiadezalnej (1961), 9(4), p. 609-29 (abstract).*
Database CAPLUS on STN, Acc. No. 1972:22491, Santi et al., Biochemistry (1971), 10(25), p. 4813-20 (abstract).*
Database CAPLUS on STN, Acc. No. 1980:639100, Wade, J. of Org. Chem. (1980), 45(26), p. 5328-5333 (abstract).*
Database CAPLUS on STN, Acc. No. 1987:571733, Gaget et al., Journal of Chromatography (1987), vol. 395, p. 597-606 (abstract).*
Database CAPLUS on STN, Acc. No. 1994:549107, Seiler, EP 609630 (1994) (abstract).*
Hintermann et al.; A Useful Modification of the Evans Auxiliary: 4-Isopropyl-5,5-diphenyloxazolidin-2-one; Helv. Chim. Acta; 1998; vol. 81; pp. 2093-2126.

Gibson et al.; A Study of 4-Substituted 5,5-Diaryl Oxazolidin-2-ones as Efficiacious Chiral Auxiliaries; Tetrahedron Letters; vol. 39, No. 37; 1998; pp. 6733-6736.
Tamura et al.; Synthetic Studies on the Key Component of the Ne Generation of Quinolonecarboxylic Acid, DU-6859.1.; TETRAHEDRON; vol. 50, No. 13; 1994; p. 3889-3904.
Bailey et al.; A short synthesis of (S)-2-(diphenylmethyl) pyrrolidene, a chiral solvating agent for NMR analysis; TETRAHEDRON; vol. 8, No. 1; 1997; pp. 149-153.
Yang et al.; Convenient synthesis of (S)-.alpha., .alpha. 'diphenyl-2-pyrrolidinemethanol; Chemical Abstracts Service; accession No. 127:278113.
Rao et al.; Enatioselective catalytic reduction of ketones with new four membered oxazaborolidines: Application to (S)-Tetramisole; TETRAHEDRON; vol. 3, No. 7; 1992; pp. 859-862.
Gawley et al.; 1-Magnesiotetrahydroisoquinolyloxazolines as Chiral Nucleophiles in Stereoselective Additions to Aldehydes:..; J. Org. Chem.; vol. 61, No. 23; 1996; pp. 8103-8112.
Delauney et al.; A New Route to Oxazolidinones; J. Chem. Socl.; 1994; pp. 3041-3042.
Alvernhe et al.; Fluorination of amino alcohols and hydroxyaziridines by Olah's reagent; Chemical Abstract Service; Accession No. 100:103081; 1983.
Wade; Preparation of Fluoro Amines by the Reaction of Aziridines with Hydrogen Fluoride in Pyridine Solution; J. Org. Chem.; vol. 45, No. 26; 1980; pp. 5328-5333.
Alvernhe et al.; Synthesis of .alpha., .beta.-fluoro amines and. alpha.-fluoro ketones by action of hydrofluoric acid on aziridines and azirines; Tetrahedron Lett.; No. 52; 1978; pp. 5203-5206.
Knölker et al.; Synthesis of Chiral Oxazolifin-2-ones and Imidazolidin-2-ones via DMAP-Catalyzed Isocyanation of Amines with Di-tert-butyl Dicarbonate; Tetrahedron Lett.; vol. 39, No. 51; 1998; pp. 9407-9410.
O'Hagan et al.; A short synthesis of (S)-alpha-(diphenylmethyl) alkyl amines from amino acids; Tetrahedron Asymmetry; vol. 10, No. 6, 1999; pp. 1189-1192.

* cited by examiner

Primary Examiner—Brian Davis
(74) Attorney, Agent, or Firm—Jacobson Holman PLLC

(57) ABSTRACT

Process for the preparation of chiral compounds of formula (I) comprising contacting a compound of formula (II) with a source of hydrogen or halide; wherein A is a chiral center; X is selected from oxygen, sulphur and nitrogen; n is selected from 0 and 1 and is equal to the valence of X less 2; B is a fragment CR 3 2; Z is hydrogen or halogen; with the proviso that when X is nitrogen, n is 1, one of R 1 and two of R 2 are hydrogen, BZ is CHPh 2, the other R 1 and R 2 do not form together a five membered heterocyclic (pyrrolidone) ring; novel intermediates, novel compounds, polymers and libraries thereof and the use thereof as fine chemicals, and compositions thereof.

9 Claims, No Drawings

PROCESS FOR PREPARING CHIRAL COMPOUNDS

The present invention relates to a process for the preparation of a class of enantiomerically pure chiral compounds, the compounds obtained thereby and novel compounds, compositions thereof and the use thereof as or in the preparation of a pharmaceutical, veterinary product, agrochemical, polymer, library of compounds and their respective intermediates.

Efficient and simple synthesis of known and novel compounds can be the key to commercial success and may also lead to further development and discoveries enabled by availability of compounds in significant purities, yields and the like. Nevertheless development of new synthetic routes is costly and time consuming, without the guarantee of success.

Tet: Asymm, 1997, 8(1), 149–153 discloses the synthesis of the corresponding excluded pyrrolidine which is a known chiral compound, but makes no reference to synthesis of analogues of any class of analogues, thus implies a unique synthesis for the compound alone.

The authors have now found, according to the present invention, that the synthesis is effective for a distinct class of compounds having potential as or in the preparation of organic fine chemicals and polymers.

We have now surprisingly found a process for synthesising a class of compounds in novel manner to produce enantiomerically pure hetero compounds.

Accordingly in a first aspect there is provided a process for the preparation of chiral compounds of formula I:

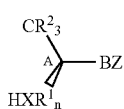

(I)

comprising contacting a compound of formula II:

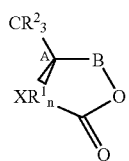

(II)

with a source of hydrogen or halide;

wherein

A is a chiral centre;

X is selected from oxygen, sulphur and nitrogen;

n is selected from 0 and 1 and is equal to the valence of X less 2;

Each $R^1$ is independently selected from hydrogen, straight chain and branched, saturated and unsaturated $C_{1-8}$ hydrocarbon optionally substituted by one or more hydroxy, halo, aryl, cyclo $C_{1-8}$ alkyl and the like;

B is a fragment $CR^3{}_2$ wherein each $R^3$ is independently selected from hydrogen, halo, azides and cyanides; straight and branched chain, saturated and unsaturated $C_{1-4}$ alkyl, alkenyl and alkynyl and aryl, each optionally substituted by hydroxy, halo, saturated or unsaturated $C_{1-4}$ alkyl, alkenyl or alkynyl, aryl, cyclo $C_{1-6}$ alkyl, carbonyl, carboxyl, amino, amido, (thio)ether, haloalkyl, silylalkyl and the like;

Z is hydrogen or halogen;

each $R^2$ is independently selected from hydrogen, straight chain and branched, saturated and unsaturated $C_{1-8}$ alkyl, optionally substituted by hydroxy, halo, aryl, cyclo $C_{1-6}$ alkyl, carbonyl, carboxyl, amino, amido, (thio)ether and the like; and one of $R^1$ and one of $R^2$ together may form an alkylene group as part of a heterocyclic ring;

with the proviso that when X is nitrogen, n is 1, one of $R^1$ and two of $R^2$ are hydrogen, BZ is $CHPh_2$, the other $R^1$ and $R^2$ do not form together a five membered heterocyclic (pyrrolidone) ring.

Preferably X is nitrogen whereby n is 1.

Preferably B is a fragment $CR^3{}_2$ wherein $R^3$ is selected from ethenyl, propenyl ethynyl and propynyl, optionally substituted phenyl, for example 4-methoxy or 4-perfluoryl alkyl phenyl, naphthyl, methyl phenyl and the like.

More preferably B is a group as hereinbefore defined wherein at least one and preferably both of $R^3$ are aryl, more preferably optionally substituted phenyl.

Preferably Z is selected from hydrogen, chloro and fluoro, more preferably hydrogen and fluoro.

Preferably $R^2$ is selected from optionally hydroxy, halo, alkoxy substituted branched and straight chain $C_{1-6}$ alkyl, including methyl, ethyl, i-propyl, i-butyl, t-butyl; and aryl including phenyl and benzyl.

Preferably X is nitrogen wherein n is 1 and $R^1$ does not form a cyclic ring with one of $R^2$, i.e. the compound is a non cyclic secondary amine, or $R^1$ is H, and $R^2$ is other than H, i.e. the compound is a primary amine.

Without being limited to this theory it is thought that the conversion according to the process of the invention proceeds via a substitution with subsequent decarboxylation or decarboxylation with subsequent quenching.

Contacting the compound of formula II as hereinbefore defined may be in the presence of a catalyst which may be homogeneous or heterogeneous, and is preferably heterogeneous, or of an agent which may be gaseous or liquid and is preferably liquid.

The catalyst may be selected from any catalyst suitable for the conversion as hereinbefore defined. Preferably the catalyst comprises a hydrogenation or fluorination catalyst or agent. A hydrogenation catalyst suitably comprises a metal adapted to catalyse a hydrogenation reaction, for example selected from the transition metals of Group VIII of the Periodic Table of the Elements, preferably selected from Pt, Pd, Ni, Co, Cu, Ru, Fe and Ag and mixtures thereof. The catalyst may be in the form of the metal(s) or salts thereof, optionally in the presence of or including additional catalytic components or catalytic supports such as C. More preferably the catalyst comprises palladium and carbon, and reaction is in the presence of gaseous hydrogen.

A fluorination agent suitably comprises a source of fluorine associated with an activating component adapted to facilitate fluorination reaction, for example liquid phase HF and a carrier, preferably HF-pyridine (Olah's reagent).

The catalyst or agent is present in catalytically or transformationally effective amount.

The process may be carried out with use of any additional solvents, and may be carried out at reduced, ambient or elevated temperature and/or pressure or a combination thereof in sequence. Gaseous reaction is preferably carried out at ambient temperature and elevated pressure in the range 1–10 atm and liquid phase reaction at ambient pressure and temperature in the range 0–20° C.

The process of the invention is preferably suitable for the preparation of pharmaceutical, veterinary product, agrochemical and polymeric compounds and libraries of such compounds, and their synthetic intermediates. It is a particular advantage of the process of the invention that such compounds may be readily prepared in which B is analogous electronically and/or sterically to characteristic groupings in known pharmaceutical, veterinary product and agrochemicals. The process therefore provides a known route to access compounds and whole ranges of new analogues, wherein the group B is as hereinbefore defined.

Alternatively the process as hereinbefore defined is suited for the preparation of metal complexes as asymmetric catalysts.

In a further aspect of the invention there is provided a class of novel enantiomerically pure chiral hetero compounds of the formula I as hereinbefore defined wherein A, B, Z and $R^1$ are as hereinbefore defined, X is N and n is 1 with the exception that $R^2$ is not phenyl or benzyl when $R^1$ is hydrogen, BH is phenyl or $CH_3$ and Z is H.

Compounds of the formula II as hereinbefore defined may be obtained commercially or prepared by known means. Akiba et al, Tetrahedron, 1994, 50 (13), 3905 discloses the preparation of a compound of formula II by cyclisation of amino alcohol with trichloromethyl chloroformate ($Cl_3COCOCl$) in the presence of triethylamine ($Et_3N$). Using this process compounds of formula II are obtained from compounds of formula III:

(III)

Intermediate compounds of formula III as hereinbefore defined may be obtained commercially or using the process, for example of Gawley and Zhang, J. Org. Chem., 1996, 61, 8103, and Itsuno et al, J. Chem. Soc., Perkin Trans. I, 1985, 2039. In this publications is taught the preparation of a compound of formula III as hereinbefore defined by reaction of a compound of formula IV:

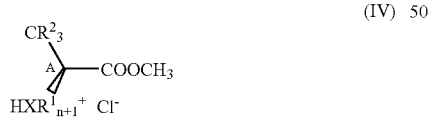

(IV)

with a compound of formula V:

$R^2MgBr$. (V)

Reaction is preferably under reflux in cold solvent.

Compounds of formula IV and V are commercially available or may be synthesised by known means.

In a further aspect of the invention there is provided a process for the preparation of enantiomerically pure chiral polymers comprising a repeating unit of the formula Ii:

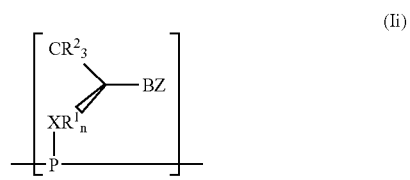

(Ii)

wherein P is derived from a polymerisable monomer or oligomer and X, $R^1$, $R^2$, B, Z and A are as hereinbefore defined.

Polymerisable monomers may be any known monomers, for example selected from monomers of thermoset and thermoplast polymers and mixtures thereof, including monomers preferably selected from the group consisting of: an epoxy resin such as an epoxy resin derived from the mono or poly-glycidyl derivative of one or more of the group of compounds consisting of aromatic diamines, aromatic monoprimary amines, aminophenols, polyhydric phenols, polyhydric alcohols, polycarboxylic acids and the like; an addition-polymerisation resin, such as a bis-maleimide resin, acrylic, vinyl or unsaturated polyester; a formaldehyde condensate resin, such as formaldehyde-phenol resin, urea, melamine or phenol resin; a cyanate resin; and an isocyanate resin; polyaromatics such as polysulphones and polyethersulphones; monomers of natural polymers including carbohydrates, polypeptides and proteins including starch, celluloses, collagen, gelatin, dextrans, alginates, chitin and chitosan; and monomers of biodegradeable and/or biocompatible polymers such as polyesters including poly(lactic acid), poly(glycolic acid), polycaprolactone and the like, polyorthoesters, polyanhydrides, polyaminoacids and azo polymers, for example for the delivery of a pharmaceutical, veterinary product or agrochemical in situ.

In a further aspect of the invention there is provided a process for the preparation of compounds of the formula Iii:

(Iii)

by the functional modification of a compound of formula I as hereinbefore defined to include additional groups $R^1$ and $R^3$ or the interconversion of one compound of formula I as hereinbefore defined to another compound of formula I as hereinbefore defined.

Preferably the compound of formula Iii as hereinbefore defined is a spatial, electronic or reactive analogue of a known pharmaceutical, veterinary product, or agrochemical, for example of a neuro active compound, such as the compound orphenadrine of formula:

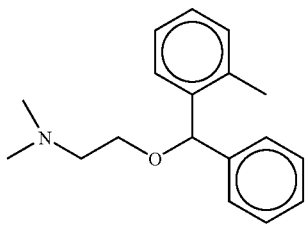

for use in treating Parkinson's Disease or of cardiovascular or gastro-intestinal drugs, immunosuppresants, respiratory agents, musculoskeletal and joint disease drugs, immunological products and vaccines, pest control agents, plant growth control agents, plant disease control agents and the like.

In a further aspect of the invention there is provided the use of one or more compounds of formula I as hereinbefore defined in the preparation of a library of compounds comprising:

reacting one or more compounds of formula I as hereinbefore defined with one or more substrates which are supported or contained in solid or liquid phase each on an individual support or within an individual vessel; and labelling the support or vessel with means to identify the synthetic history of the supported or contained compound.

The process for preparing a library of compounds may employ any techniques as known in the art of combinatorial chemistry.

In a further aspect of the invention there is provided a process for the preparation of a library of compounds of formula I as hereinbefore defined comprising:

reacting one or more compounds of formula IV as hereinbefore defined with a plurality of compounds of formula V as hereinbefore defined, and converting via compounds of formula II as hereinbefore defined to compounds of formula I as hereinbefore defined; and optionally labelling the support or vessel with means to identify the synthetic history of the supported or contained compound.

In a further aspect of the invention there is provided a library of compounds of formula I, II or III as hereinbefore defined.

Preferably the library of compounds is suitable for any of the hereinbefore defined uses. The library may be provided in the form of a kit of sample boxes for the intended use. The library may contain two or more compounds, for example ten or more compounds, preferably comprises 50–1,000 compounds of any given formula as hereinbefore defined, optionally including synthetic history identification.

In a further aspect of the invention there is provided a pharmaceutical, veterinary product or agrochemical composition comprising a compound of formula I as hereinbefore defined or derivatives thereof together with suitable diluents, adjuvants, carriers and the like.

The invention is now illustrated in non limiting manner with reference to the examples and Table 1.

| Ex | I | Z | R2 | R2 | R2 | R3 | R3 | IV ester | III alcohol | II oxazolidinone |
|---|---|---|---|---|---|---|---|---|---|---|
| 1.1 | 4 | H | CH3 | CH3 | H | Ph | Ph | Methyl 1 | butanol 2 | 3 |
| 1.2 | 8 | H | CH2Ph | H | H | Ph | Ph | ethyl 5 | Butanol 6 | 7 |
| 1.3 | 12 | H | H | H | H | Ph | Ph | Methyl 9 | Butanol 10 | 11 |
| 1.4 | 15 | H | C2H5 | CH3 | H | Ph | Ph | Methyl | Pentanol 13 | 14 |
| 1.5 | 18 | H | IPr | H | H | Ph | Ph | Methyl | Pentanol 16 | 17 |
| 2.1 | 19 | F | C2H5 | CH3 | H | Ph | Ph | Methyl | 13 | 14 |
| 2.2 | 20 | F | iPr | H | H | Ph | Ph | Methyl | 16 | 17 |
| 2.3 | 21 | F | -pyrrolidine- | | H | Ph | Ph | Tet: | Tet: | Tet: |

EXAMPLES

Synthesis of Novel Chiral Amines

1. Chiral Amines wherein Z is H 1.1 Synthesis of (S)-2-amino-1,1-diphenyl-3-methyl-1-butane (2)

Synthesis of (S)-2-amino-1,1-diphenyl-3-methyl-1-butane (2)

The title compound (2) was readily prepared by the addition of L-valine methyl ester hydrochloride (1) to phenylmagnesium bromide, as depicted in Scheme 1, following the modified method described by Gawley[i] and Zhang (1996), and Itsuno[ii] et al. (1985).

Scheme 1

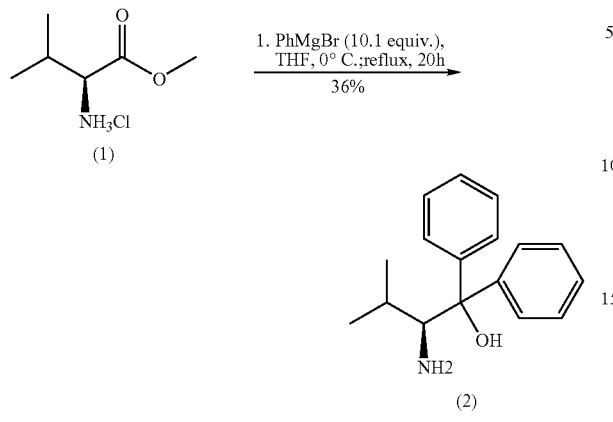

Purification over silica gel, gave (2) as a white solid in moderate yield (36%).

Synthesis of (S)-4-isopropyl-5,5-diphenyl-2-oxazolidinone (3)

In the event, the title compound (3) was readily prepared by the cyclisation of aminoalcohol (2) with trichloromethyl chloroformate (Cl$_3$COCOCl) in the presence of triethylamine (Et$_3$N), as shown in Scheme 2, following the method described by Akiba[iii] et al. (1994).

Scheme 2

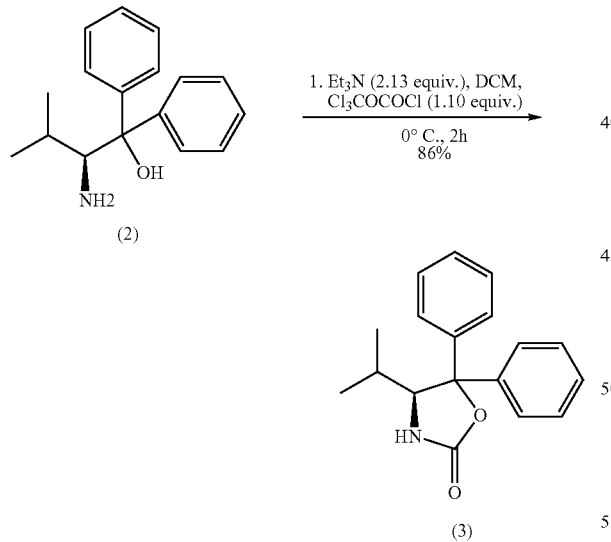

Upon work-up, the solid residue was loaded on to a sintered funnel and then washed with diethyl ether to obtain the title compound (3) as a white solid in good yield (86%).

Synthesis of (S)-2-amino-3-methyl-1,1-diphenylbutane (4)

In the presence of a catalytic amount of palladium on activated carbon, 2-oxazolidinone (3) was finally submitted to the hydrogenation in a mixture of AcOH and MeOH under 4–5 atm. pressure, as illustrated in Scheme 3.

Scheme 3

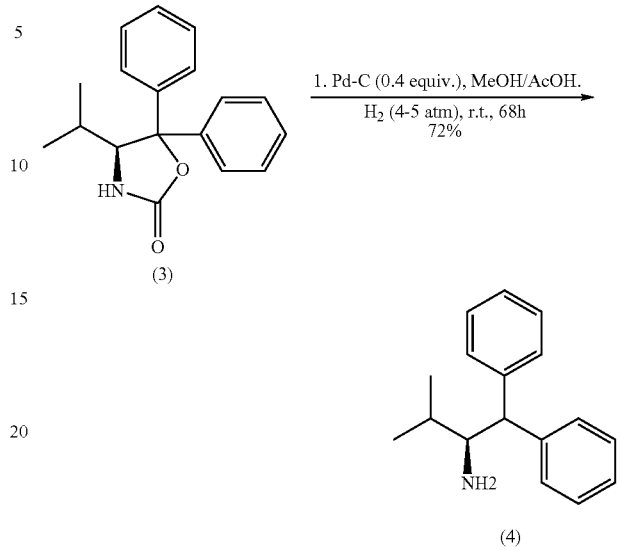

Upon filtration and re-crystallisation from petroleum ether, the title compound (4) was generated as a white solid in good yield (72%).

1.2 Synthesis of (S)-2-amino-1,1,3-triphenyl-1-propane (6)

Synthesis of (S)-2-amino-1,1,3-triphenyl-1-propanol (6)

The title compound (6), following the modified literature methods of Itsuno[ii,iv] et al. (1985), Weber[v] et al. (1995) and Dammast and Reiβig[vi] (1993), was readily prepared by the portionwise addition of L-phenylalanine ethyl ester hydrochloride (5) to phenylmagnesium bromide, as depicted in Scheme 4.

Scheme 4

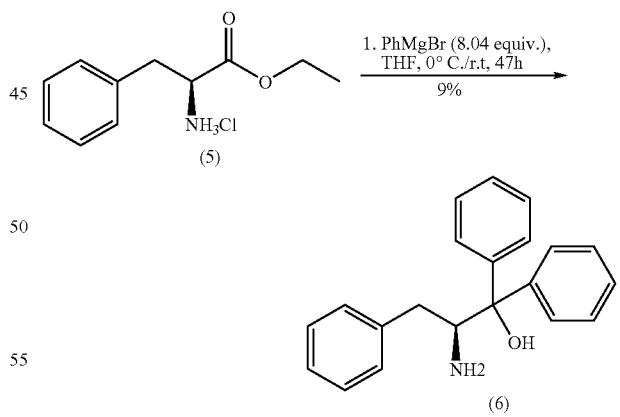

Recrystallisation gave the title compound (6) as a white solid in low yield (9%).

Synthesis of (S)-4-benzyl-5,5-diphenyl-2-oxazolidinone (7)

In the event, the title compound (7) was readily prepared by the cyclisation of aminoalcohol (6) with trichloromethyl chloroformate (Cl$_3$COCOCl) in the presence of triethylamine (Et$_3$N), as shown in Scheme 5, following the method described by Akiba[iii] et al. (1994).

Scheme 5

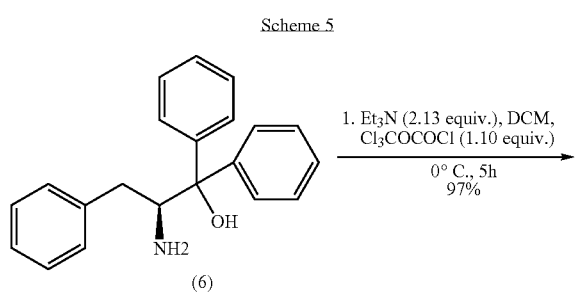

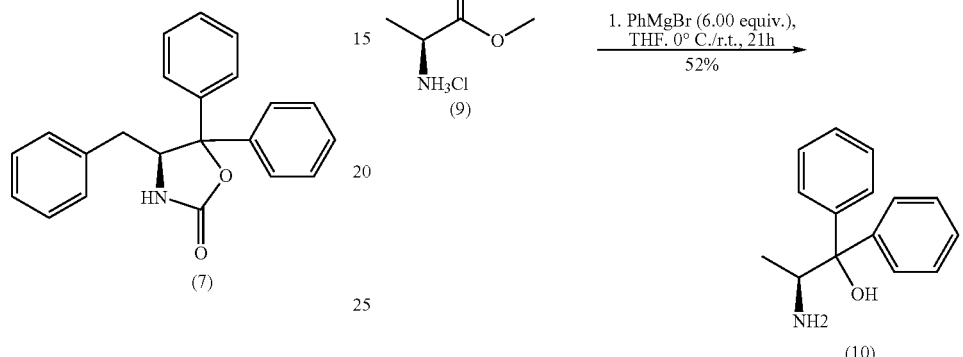

Upon work-up, the solid residue was loaded on to a sintered funnel and then washed with diethyl ether to obtain the title compound (7) as a white solid in excellent yield (97%).

Synthesis of (S)-2-amino-1,1,3-triphenyl-propane (8)

In the presence of a catalytic amount of palladium on activated carbon, 2-oxazolidinone (7) was finally subjected to the hydrogenation in a mixture of AcOH and MeOH under 4–5 atm. pressure, as illustrated in Scheme 6.

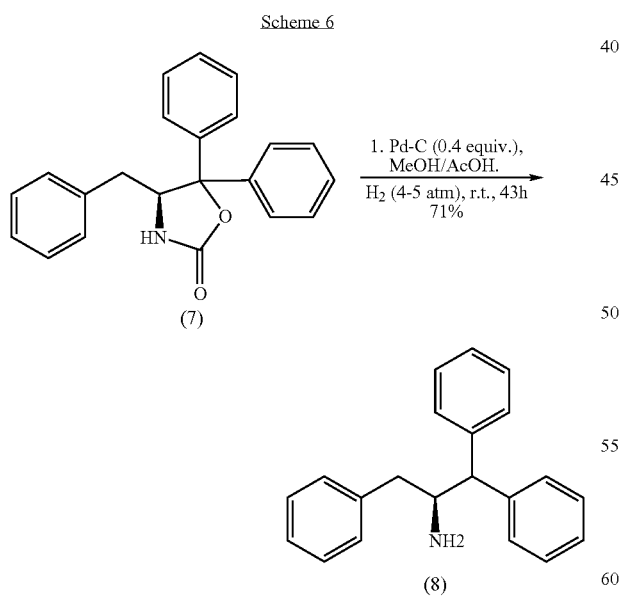

Upon filtration and purification over silica gel, eluting with a 3:7 and 4:6 mixture of AcOEt and petrol, the title compound (8) was obtained as a light-brown solid in good yield (71%).

1.3 Synthesis of (S)-2-amino-1,1-diphenyl-1-propanol (10)

Synthesis of (S)-2-amino-1,1-diphenyl-1-propanol (10)

The title compound (10), following the literature methods of Itsuno[ii] et al. (1985), Weber[v] et al. (1995) and Dammast[vi] and Reißig (1993), was readily prepared by the portionwise addition of L-alanine methy ester hydrochloride (9) to phenylmagnesium bromide, as depicted in Scheme 7.

Scheme 7

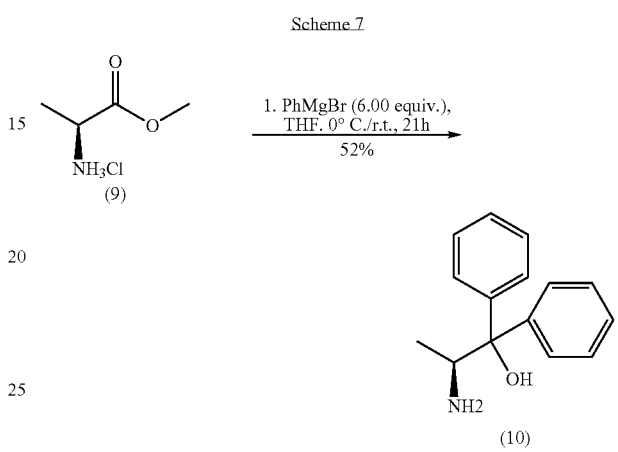

Flash column chromatography, eluting with dichloromethane and then further elution with a mixture of AcOEt and petrol, ranging from 15% up to 100%, gave the title compound (10) as a white solid in moderate yield (52%).

Synthesis of (S)-4-methyl-5,5-diphenyl-2-oxazolidinone (11)

In the event, the title compound (11) was readily prepared by the cyclisation of aminoalcohol (10) with trichloromethyl chloroformate ($Cl_3COCOCl$) in the presence of triethylamine ($Et_3N$), as shown in Scheme 8, following the method described by Akiba[iii] et al. (1994).

Scheme 8

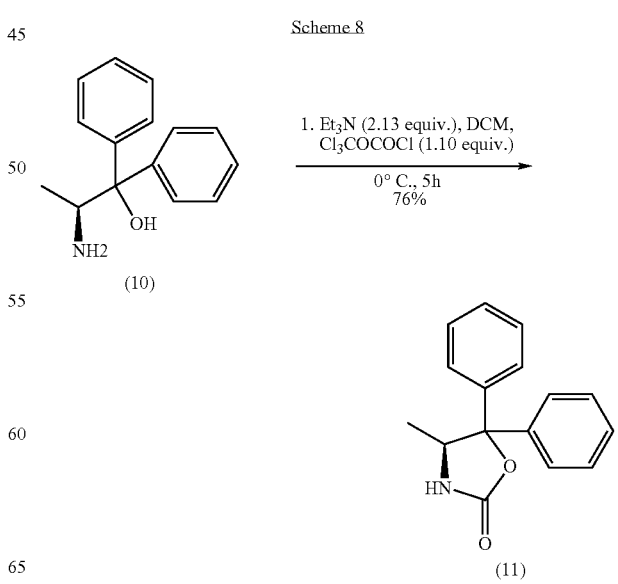

Upon work-up, the solid residue was loaded on to a sintered funnel and then washed with diethyl ether to obtain the title compound (11) as a white solid in good yield (76%).

Synthesis of (S)-2-amino-1,1-diphenyl-propane (12)

In the presence of a catalytic amount of palladium on activated carbon, 2-oxazolidinone (11) was finally subjected to the hydrogenation in a mixture of AcOH and MeOH under 4–5 atm. pressure, as illustrated in Scheme 9.

Scheme 9

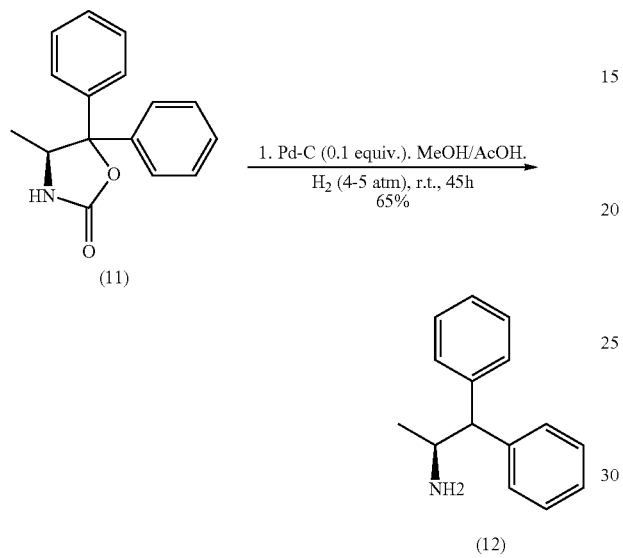

Upon filtration and purification by dry-flash column chromatography, eluting first with AcOEt, and then with a mixture of MeOH and AcOEt, ranging from 5% up to 30%, gave the title compound (12) as a white solid in moderate yield (71%).

Experimental 1.1 (S)-2-amino-1,1-diphenyl-3-methyl-1-butanol (2)

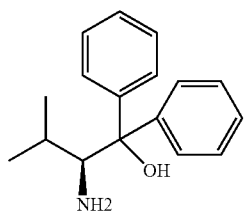

L-Valine methyl ester hydrochloride (9.9 g, 59.06 mmol) was added portionwise to a 1.0 M solution of phenylmagnesium bromide (108.8 g, 0.6 mol) in THF at 0° C. and heated at reflux for 20 h. After quenching with crushed ice and NH$_4$Cl salt, the organic layer was separated, washed with brine and concentrated under reduced pressure. The resulting solid was treated with HCl (2.0 M, 100 ml) and then evaporated to dryness under reduced pressure. Impurities precipitated out as a white solid, when the amine hydrochloride salt was dissolved in hot MeOH and allowed to cool to room temperature. After removing the impurities by filtration, the filtrate was made basic with KOH (1.0 M) and the organics were extracted into diethyl ether (4×100 ml). Combined organic extracts were dried over MgSO$_4$ and concentrated under reduced pressure to obtain a crude product as a light brown solid. Purification over silica gel, eluting with a 1:4 and 1:1 mixture of ethyl acetate and petrol gave the title compound (2) (5.42 g, 36%) as a white solid. m.p. 90–92° C. (lit$^i$ 94–95° C.). [α]$_D^{25}$=−107.92° (c, 0.0424 in CHCl$_3$) (lit$^{ii}$: −127.7° (c, 0.639 in CHCl$_3$). δ$_H$ 0.81 (3H, d, $^3J$=6.90 Hz, CH$_3$), 0.85 (3H, d, $^3J$=7.20 Hz), 1.67 (1H, ds, $^3J$=1.80 and 6.90 Hz, CH-Me$_2$), 3.76 (1H, d, $^3J$=2.10 Hz, CH—NH$_2$), 7.04–7.58 (10H, m, Ar). δ$_C$ 16.3 and 23.2 (CH$_3$), 28.1 (CH—Me$_2$), 60.4 (CH—NH$_2$), 79.9 (C—OH), 125.7, 126.1, 126.5, 126.8, 128.2 and 128.6 (o-, m- and p-Ar), 145.1 and 148.2 (α-Ar. Anal. Calcld. for C$_{17}$H$_{21}$NO: C 79.96; H 8.29; N 5.48. Found: C 79.80; H 8.15; N 5.39. ir 3338 (OH and NH$_2$). m/e (CI—CH$_4$) 256 (MH$^+$, 14%), 72 (100%).

(S)-4-isopropyl-5,5-diphenyl-2-oxazolidinone (3)

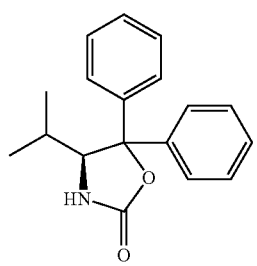

Trichloromethyl chloroformate (2.71 g, 13.7 mmol) was added to a mixture of (S)-2-amino-3-methyl-1,1-diphenyl-1-butanol (2) (3.18 g, 12.45 mmol) and triethylamine (2.68 g, 26.52 mmol) in CH$_2$Cl$_2$ at 0° C. The reaction mixture was stirred for 2 h at the same temperature and then poured into a brine solution (250 ml). The aqueous layer was made basic with NaOH pellets and organic products were extracted into AcOEt (5×200 ml). Combined organic extracts were dried over MgSO$_4$ and concentrated under reduced pressure. The resulting crude product was washed with diethyl ether to obtain the title compound (3) (3.03 g, 86%) as a white solid. m.p. 250–251° C. (lit$^i$ 250–251° C.). [α]$_D^{25}$=−201.59° (c, 0.0252 in DMSO). δ$_H$ (DMSO-d$_6$) 0.51 (3H, d, $^3J$=6.60 Hz, CH$_3$), 0.92 (3H, d, $^3J$=7.20 Hz, CH$_3$), 1.86 (1H, ds, $^3J$=2.10 and 6.60 Hz, CH—Me$_2$), 4.46 (1H, d, $^3J$=6.5 Hz, CH—NH$_2$), 7.24–7.72 (10H, m, Ar—H), 8.14 (1H, s, NH). δ$_C$ 15.2 and 20.9 (CH$_3$), 29.8 (CH), 64.9 (CH—NHCO), 88.4 (C—O), 125.8, 126.2, 127.9, 128.4, 128.8 and 129.1 (Ar), 140.5 and 146.1 (α-Ar), 158.1 (C=O). Ir 3295 (NH$_2$), 1765 and 1745 (C=O). m/e (CI—NH$_3$) 282 (MH$^+$, 25%), 299 (MNH$_4^+$, 8%), 238 (96%), 223 (100%), 72 (100%).

(S)-2-amino-3-methyl-1,1-diphenylbutane (4)

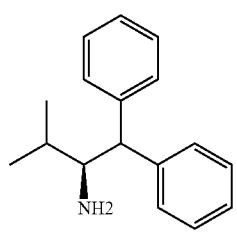

A solution of (S)-4-isopropyl-5,5-diphenyl-2-oxazolidinone (3) (2.9 g, 10.31 mmol) in MeOH/AcOH and a 10% Pd (435 mg, 4.09 mmol) on activated carbon was shaken for 68 h under 4–5 atm pressure of hydrogen at room temperature. The catalyst was filtered off over Hyflo Super Cell and organic solvents were evaporated under reduced pressure. The resulting residue was treated with HCl (2.0 M, 50 ml), stirred for 2 h at room temperature, made basic with NaOH pellets, and saturated with $K_2CO_3$ and NaCl. Organic compounds were then extracted into AcOEt (3×100 ml), dried over $MgSO_4/K_2CO_3$ and concentrated under reduced pressure to obtain a crude product. Re-crystallisation from petroleum ether gave the title compound (4) (1.79 g, 72%) as a light-brown solid. m.p. 71–72° C. $[\alpha]_D^{25}=-4.19°$ (c, 0.1097 in $CHCl_3$). $\delta_H$ 0.78 (3H, d, $^3J$=6.60 Hz, $CH_3$), 0.91 (3H, d, $^3J$=7.20 Hz, $CH_3$), 1.26 (2H, broad s, $NH_2$), 1.62 (1H, ds, $CHMe_2$), 3.45 (1H, dd, $^3J$=10.5 and 2.40 Hz, CH—$NH_2$), 3.70 (1H, d, $^3J$=10.5 Hz, CH—$Ph_2$), 7.00–7.40 (10H, m, Ar—H). $\delta_C$ 14.2 and 21.5 (CH3), 28.9 (CH—$Me_2$), 58.1 and 58.9 (CH—$NH_2$ and CH—$Ph_2$), 126.5, 126.7, 128.2, 128.5, 128.8 and 129.0 (o-, m- and p-Ar), 143.5 (2×α-Ar). Anal. Calcld for $C_{17}H_{21}N$: C 85.30; H 8.84; N 5.85. Found: C 85.12; H 8.91; N 5.96. ir 3361 ($NH_2$). m/e (CI—$CH_4$) 240 (MH$^+$, 8%), 72 (100%).

1.2 (S)-2-Amino-1,1,3-triphenyl-1-propanol (6)

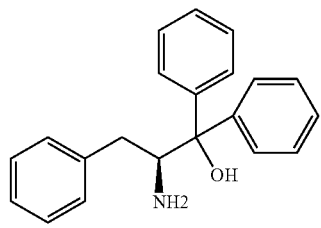

(6)

L-Phenylalanine ethyl ester hydrochloride (9.9 g, 43.1 mmol) was added portionwise to a 1.0 M solution of phenylmagnesium bromide (63.46 g, 0.35 mol) in THF at 0° C. and stirred for 20 h at room temperature. After quenching with crushed ice and concentrated HCl, the aqueous layer was separated and evaporated to dryness under reduced pressure. The resulting solid was washed with diethyl ether and AcOEt to obtain a white gummy HCl-salt. Upon basification with NaOH (1.0 M), organic products were extracted into diethyl ether and AcOEt, dried over $MgSO_4$, and concentrated under reduced pressure to obtain a crude product. Re-crystallisation from a mixture of AcOEt and diethyl ether gave the title compound (6) (1.16 g, 9%) as a white solid. m.p. 141–142° C. (lit$^{ii}$ 144–145° C.; lit$^{vi}$ 143–144° C.). $[\alpha]_D^{25}=-88.40°$ (c, 0.0181 in $CHCl_3$) (lit$^{ii}$: −88.50° (c, 0.604 in $CHCl_3$); lit$^{vi}$: −94.3° (c, 2.30 in $CHCl_3$). $\delta_H$ 2.38 (1H, dd, $^3J$=10.8 Hz, $^2J$=13.8 Hz, $CH_2$—Ph), 2.58 (1H, dd, $^3J$=2.4 Hz, $^2J$=13.8 Hz, $CH_2$—Ph), 4.11 (1H, dd, $^3J$=2.4 Hz, $^3J$=10.8 Hz, CH—$NH_2$), 7.06–7.62 (15H, m, Ar—H). $\delta_C$ 36.9 ($CH_2$—Ph), 58.4 (CH—$NH_2$), 78.7 (C—OH), 125.6, 126.0, 126.6, 126.7, 126.9, 128.4, 128.7, 128.8 and 129.3 (o-, m- and p-Ar), 139.8, 144.5 and 147.0 (α-Ar). ir 3365 ($NH_2$), 3320 (OH). m/e (CI—$NH_3$) 304 (MH$^+$, 30%), 271 (100%).

(S)-4-benzyl-5,5-diphenyl-2-oxazolidinone (7)

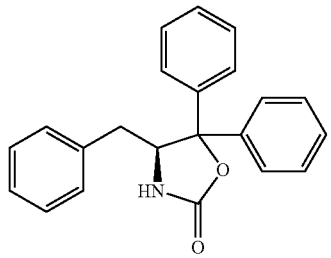

(7)

Trichloromethyl chloroformate (718 mg, 3.63 mmol) was added to a mixture of (S)-2-amino-1,1,3-triphenyl-1-propanol (6) (1.00 g, 3.30 mmol) and triethylamine (710 mg, 7.02 mmol) in $CH_2Cl_2$ at 0° C. The reaction mixture was stirred for 5 h at the same temperature and then poured into a brine solution (150 ml). The aqueous layer was made basic with powdered $K_2CO_3$ and organics were extracted into dichloromethane (3×50 ml). The combined organic extracts were dried over $MgSO_4/K_2CO_3$ and concentrated under reduced pressure. The resulting crude product was washed with diethyl ether to obtain the title compound (7) (1.06 g, 97%) as a white solid. m.p. 259–261° C. (lit ? ° C.). $[\alpha]_D^{25}=-241.94°$ (c, 0.0211 in DMSO), $\delta_H$ (DMSO-$d_6$) 2.18 (1H, dd, $^3J$=10.8 Hz, $^2J$=13.8 Hz, $CH_2$—Ph), 2.52 (1H, dd, $^3J$=3.6 Hz, $^2J$=13.8 Hz, $CH_2$—Ph), 4.67 (1H, dd, $^3J$=3.6 Hz, $^3J$=10.8 Hz, CH—$NH_2$), 6.90–7.60 (15H, m, Ar—H). $\delta_C$ 44.2 ($CH_2$—Ph), 50.5 (CH—NH), 94.1 (C—O), 130.5, 130.9, 131.5, 132.6, 132.8, 133.0, 133.1, 133.3 and 133.4 (o-, m- and p-Ar), 141.1, 143.4 and 146.5 (α-Ar), 163.7 (C=O), ir 3248 ($NH_2$), 1760 and 1725 (C=O). m/e (CI—$NH_3$) 330 (MH$^+$, 5%), 347 ($MNH_4^+$, 6%), 196 (100%).

(S)-2-Amino-1,1,3-triphenyl-propane (8)

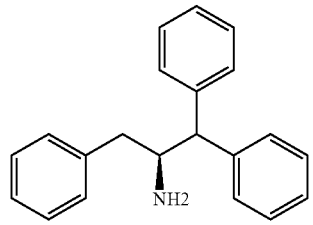

(8)

A solution of (S)-4-benzyl-5,5-diphenyl-2-oxazolidinone (7) (940 mg, 2.85 mmol) in MeOH/AcOH and a 10% Pd (121 mg, 1.14 mmol) on activated carbon was shaken for 43 h under 4–5 atm pressure of hydrogen at room temperature. The catalyst was filtered off over Hyflo Super Cell and organic solvents were evaporated under reduced pressure. The resulting residue was treated with HCl, stirred for 2 h at room temperature, made basic with NaOH pellets, and saturated with $K_2CO_3$ and NaCl. Organics were then extracted into dichloromethane (4×50 ml), dried over $MgSO_4/K_2CO_3$ and concentrated under reduced pressure to obtain a crude product. Purification over silica gel, eluting with a 3:7 and 4:6 mixture of AcOEt and petroleum ether, gave the title compound (8) (584 mg, 71%) as a light-brown solid. m.p. 71–72° C. $[\alpha]_D^{25}=-8.03°$ (c, 0.1046 in $CHCl_3$). $\delta_H$ 1.21 (2H, broad s, $NH_2$), 2.29 (1H, dd, $^3J$=9.6 Hz, $^2J$=13.5 Hz, $CH_2$—Ph), 2.79 (1H, dd, $^3J$=2.1 Hz, $^2J$=13.2 Hz, $CH_2$—

Ph), 3.71 (1H, d, $^3J$=9.9 Hz, CH—Ph$_2$), 3.81 (1H, ddd, $^3J$=2.7, 9.9 and 12.6 Hz, CH—NH$_2$), 7.06–7.33 (15H, m, Ar—H), $\delta_C$ 41.9 (CH$_2$—Ph), 55.7 and 59.7 (CH—Ph$_2$ and CH—NH$_2$), 126.3, 126.5, 126.6, 128.1, 128.2, 128.4, 128.7, 128.8 and 129.1 (o-, m- and p-Ar), 139.7, 142.6 and 143.1 (α-Ar). ir 3387 (NH$_2$). m/e (CI—NH$_3$) 288 (MH$^+$, 100%).

1.3 (S)-2-Amino-1,1-diphenyl-1-propanol (10)

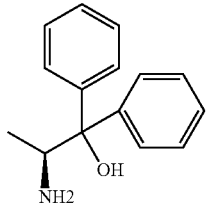
(10)

L-Alanine methyl ester hydrochloride (9.9 g, 70.9 mmol) was added portionwise to a 1.0 M solution of phenylmagnesium bromide (78.0 g, 0.43 mol) in THF at 0° C. and then heated under reflux for 21 h. The reaction mixture was cooled to 0° C., quenched with dropwise addition of saturated NH$_4$Cl, and stirred for 1 h. After collecting insoluble products through the Buchner funnel, organic products were extracted into AcOEt (3×100 ml). The combined organic extracts were dried over K$_2$CO$_3$/MgSO$_4$, and concentrated under reduced pressure to obtain a crude product. Impurities were washed with dichloromethane over silica gel by means of dry-flash column chromatography, further elution with a mixture of AcOEt and petrol, ranging from 20% up to 100%, gave the title compound (10) (1.16 g, 9%) as a white solid. m.p. 100–101° C. (lit$^{ii,v}$ 100–102° C.). $[\alpha]_D^{25}$=−85.59° (c, 0.0362 in CHCl$_3$) (lit$^{ii}$: −82.38° (c, 0.814 in CHCl$_3$; lit$^v$: −85.9° (c, 2.77 in CHCl$_3$). $\delta_H$ 0.94 (3H, d, $^3J$=6.30 Hz, CH$_3$), 1.23 (2H, broad s, NH$_2$), 4.15 (1H, q, $^3J$=6.30 Hz, CH—NH$_2$), 4.25 (1H, broad s, OH), 7.10–7.66 (10H, m, Ar—H). $\delta_C$ 17.4 (CH$_3$), 52.1 (CH—NH$_2$), 78.7 (C—OH), 125.7, 126.1, 126.6, 126.9, 128.2 and 128.7 (o-, m- and p-Ar), 145.0 and 147.2 (α-Ar). Anal. Calcld. for C$_{15}$H$_{17}$NO: C 79.26; H 7.54; N 6.16. Found: C 79.30; H 7.66; N 6.27. ir 3432 (OH), 3389 (NH$_2$). m/e (CI—NH$_3$) 228 (MH$^+$, 100%).

(S)-4-Methyl-5,5-diphenyl-2-oxazolidinone (11)

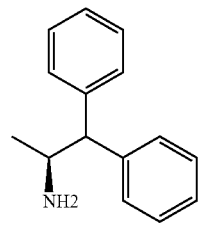
(11)

Trichloromethyl chloroformate (6.37 g, 32.19 mmol) was added to a mixture of (S)-2-amino-1,1-diphenyl-1-propanol (10) (6.65 g, 29.26 mmol) and triethylamine (6.31 g, 62.3 mmol) in CH$_2$Cl$_2$ at 0° C. The reaction mixture was stirred for 5 h at the same temperature, poured into a brine solution (150 ml), and diluted with more dichloromethane. After collecting insoluble impurities through the Buchner funnel, the organic layer was separated and the aqueous layer was washed once with a mixture of dichloromethane and AcOEt. The combined organic extracts were dried over MgSO$_4$/K$_2$CO$_3$ and concentrated under reduced pressure. The resulting crude product was washed with diethyl ether, water, AcOEt and diethyl ether again, to obtain the title compound (11) (5.67 g, 76%) as a white solid. m.p. 264–266° C. $[\alpha]_D^{25}$=−279.71° (c, 0.0414 in DMSO). $\delta_H$ 0.82 (3H, d, $^3J$=6.30 Hz, CH$_3$), 4.65 (1H, q, $^3J$=6.0 Hz, CH—NH$_2$), 7.10–7.70 (10H, m, Ar—H), 7.93 (1H, broad s, NH). $\delta_C$ 19.6 (CH$_3$), 55.9 (CH—NH$_2$), 85.6 (C—O), 126.3, 126.4, 128.1, 128.6, 128.8 and 129.1 (o-, m- and p-Ar), 140.6 and 144.2 (α-Ar), 157.6 (C=O). ir 3254 (NH), 1745 and 1725 (C=O). m/e (CI—NH$_3$) 254 (MH$^+$, 9%), 271 (MNH$_4^+$, 55%), 52 (100%).

(S)-2-Amino-1,1-diphenyl-propane (12)

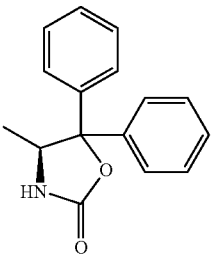
(12)

A suspension of (S)-4-methyl-5,5-diphenyl-2-oxazolidinone (11) (3.52 g, 13.90 mmol) in MeOH/AcOH and a 10% Pd (148 mg, 1.39 mmol) on activated carbon was shaken for 45 h under 4–5 atm pressure of hydrogen at room temperature. The catalyst was filtered off over Hyflo Super Cell and organic solvents were evaporated under reduced pressure. The resulting residue was treated with HCl (2M, 100 ml), stirred overnight at room temperature, made basic with NaOH pellets, and saturated with K$_2$CO$_3$. The organics were then extracted into diethyl ether (3×100 ml), dried over MgSO$_4$/K$_2$CO$_3$ and concentrated under reduced pressure to obtain a crude product. Impurities were washed with AcOEt over silica gel by means of dry-flash column chromatography, and then further elution with a mixture of MeOH and AcOEt, ranging from 5% up to 30%, gave the title compound (12) (1.90 g, 65%) as a white solid. m.p. 76–77° C. $[\alpha]_D^{25}$=−19.32 (c, 0.10765 in CHCl$_3$). $\delta_H$ 1.04 (3H, d, $^3J$=6.30 Hz, CH$_3$), 1.31 (2H, broad s, NH$_2$), 3.55 (1H, d, J=9.90 Hz, CH—Ph$_2$), 3.73 (1H, dq, $^3J$=6.30 and 10.20 Hz, CH—NH$_2$), 7.10–7.40 (10H, m, Ar—H). $\delta_C$ 22.4 (CH$_3$), 50.3 (CH—NH$_2$), 62.4 (CH—Ph$_2$), 126.5, 126.8, 128.2, 128.5, 128.7 and 129.0 (o-, m- and p-Ar), 143.3 and 143.7 (α-Ar). Anal. Calcld for C$_{15}$H$_{17}$NO: C 85.26; H 8.11; N 6.63. Found: C 85.10; H 8.08; N 6.36. ir 3343 (NH$_2$). m/e (CI—NH$_3$) 212 (MH$^+$, 100%).

1.4 (S)-α-(Diphenylmethyl)-α-[(R)-1-methylpropyl)-methylamine (15)

(2S,3R)-2-Amino-1,1-diphenyl-3-methylpentan-1-ol (13)

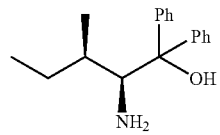
13

A 1 M solution of phenylmagnesium bromide (49.0 g, 0.27 mol) in THF was added dropwise to (S)-isoleucine methyl ester hydrochloride (9.8 g, 54.0 mmol) at 0° C. and then stirred for 17 h at room temperature. The reaction mixture was cooled to 0° C., quenched with dropwise addition of saturated NH₄Cl and then diluted with AcOEt and water until partition occurred. Organic products were extracted into AcOEt (3×50 ml), dried over MgSO₄/K₂CO₃ and concentrated to obtain a crude product. The crude product was dissolved in diethyl ether (150 ml), treated with concentrated HCl until all of the amine was converted to its HCl salt. The amine-HCl salt was stirred overnight, diluted with water until partition occured. The non-basic organics were extracted into diethyl ether (5×100 ml) and then the aqueous layer was made basic with NaOH pellets. After stirring for 4 h, organic products were extracted into AcOEt (4×75 ml) and dried over MgSO₄/K₂CO₃. Concentration gave a crude product (6.1 g, 42%) as a pale yellow solid. This contaminated with the amino ester derived from the starting material, however was used for the next step without further purification. A small amount of the crude product (1.1 g) was purified over silica gel by means of dry-flash column chromatography, eluting first with CH₂Cl₂, then with a mixture of AcOEt and petrol, increasing from 40% up to 80%. From this, a pure amino alcohol 13 (654 mg, 60%) was obtained as a white amorphous solid. m.p. 128–129° C. (lit 135–136° C.). $[\alpha]_D^{25}=-128.17°$ (c, 4.26 in CHCl₃) (lit: −124.1° (c, 1.23 in CHCl₃)). $\delta_H$ 0.72 (3H, t, J=7.2 Hz, CH₃), 0.94 (3H, d, J=6.9 Hz, CH₃), 0.80–1.10 (1H, m, CH₂), 1.40–1.60 (1H, m, CH), 1.76–1.94 (1H, m, CH₂), 0.60–2.10 (3H, OH and NH₂), 3.85 (1H, d, J=1.5 Hz, CH—NH₂), 7.10–7.70 (10H, m, Ar—H). $\delta_C$ 12.1 (CH₃—CH₂), 18.7 (CH₃—CH), 22.5 (CH₂), 34.8 (CH—Me), 60.9 (CH—NH₂), 79.6 (C), 125.5, 125.9, 126.1, 126.5, 127.8, 128.2, 144.9, 147.9 (Ar). $\nu_{max}$ (cm⁻¹): 3343, 3279 (N—H and O—H), 3085, 3023 (Ar C—H), 2959, 2926, 2873 (methyl and methylene C—H), 1589, 1491, 1447 (Ar C=C). m/e 270 (MH⁺, 4%), 252 (20%), 86 (100%).

(S)-4-[(R)-1-Methylpropyl]-5,5-diphenyl-2-oxazolidinone 14

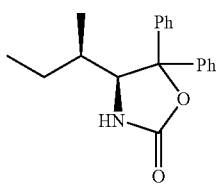

14

Trichloromethyl chloroformate (5.4 g, 27.3 mmol) was added to a mixture of (S)-2-amino-1,1-diphenyl-3-methyl-pentan-1-ol 13 (4.97 g of 60%, 11.1 mmol) and triethylamine (5.3 g, 52.0 mmol) in CH₂Cl₂ at 0° C. The reaction mixture was stirred for 3 h at 0° C., then allowed to warm to room temperature for 18 h. The mixture was then washed with HCl (3×100 ml) and water (2×100 ml) and dried over MgSO₄. Concentration gave a crude product, which was washed with diethyl ether to afford the title compound 14 (2.7 g, 83%) as a white amorphous solid. m.p. 221–223° C. $[\alpha]_D^{25}=-243.9°$ (c, 4.33 in CHCl₃). $\delta_H$ 0.41 (3H, t, J=7.2 Hz, CH₃), 0.80 (3H, d, J=6.9 Hz, CH₃), 0.80–0.96 (1H, m, CH₂), 1.18–1.32 (1H, m, CH—Me), 1.34–1.50 (1H, m, CH₂), 4.27 (1H, d, J=3.6 Hz, CH—NH), 6.98 (1H, s, NH), 7.10–7.50 (10H, m, Ar—H). $\delta_C$ 11.3 (CH₃—CH₂), 17.2 (CH₃—CH), 22.7 (CH₂), 36.3 (CH—Me), 66.1 (CH—NH), 89.5 (C), 125.9, 126.5, 127.7, 128.0, 128.3, 128.6, 139.3, 144.0 (Ar), 159.1 (C=O). $\nu_{max}$ (cm⁻¹): 3281, 3162 (N—H), 3058 (Ar C—H), 2980, 2960, 2933, 2877 (methyl and methylene C—H), 1760, 1725 (C=O), 1493, 1448 (Ar C=C), 1243 (C—O). m/e 313 (MNH₄⁺, 6%), 296 (MH⁺, 8%), 237 (100%).

(S)-α-(Diphenylmethyl)-α-[(R)-1-methylpropyl]-methylamine 15

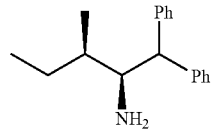

15

A suspension of (S)-4-sec-butyl-5,5-diphenyl-2-oxazolidinone 17 (2.3 g, 7.9 mmol) in MeOH/AcOH and a 10% Pd (100 mg, 0.9 mmol) on activated carbon was shaken for 47 h under 4–5 atm pressure of hydrogen at room temperature. The catalyst was filtered off over Hyflo Super Cell and solvents were evaporated. The resulting residue was treated with HCl until all of the amine was converted to its HCl salt, stirred overnight at room temperature and diluted with water until partition occurred. The non-basic organics were extracted into diethyl ether (2×100 ml) and the aqueous layer was made basic with NaOH pellets. Organic compounds were then extracted into CH₂Cl₂ (5×100 ml) and the combined extracts were dried over MgSO₄. Concentration gave a crude product, which was purified over silica gel by means of dry-flash column chromatography, eluting first with CH₂Cl₂, then with a mixture of AcOEt and petrol, ranging from 50% up to 70%. This afforded the title compound 15 (1.4 g, 71%) as a white amorphous solid. m.p. 59–61° C. $[\alpha]_D^{25}=-13.7°$ (c, 4.80 in CHCl₃). $\delta_H$ 0.76 (3H, t, J=7.5 Hz, CH₃), 0.96 (3H, d, J=6.9 Hz, CH₃), 1.00–1.18 (3H, broad s and m, NH₂ and CH₂), 1.28–1.42 (1H, m, CH—Me), 1.50–1.70 (1H, m, CH₂), 3.50 (1H, dd, J=10.5 and 2.40 Hz, CH—NH₂), 3.87 (1H, d, J=10.5 Hz, CH—Ph₂), 7.10–7.40 (10H, m, Ar—H). $\delta_C$ 11.2 (CH₃—CH₂), 16.7 (CH₃—CH), 20.4 (CH₂), 34.8 (CH—Me), 56.4 (CH—Ph₂), 58.4 (CH—NH₂), 125.2, 125.4, 127.0, 127.4, 127.5, 127.7 (Ar). Accurate mass (CI): Found 254.189998; Calculated for (MH⁺) C₁₈H₂₄N 254.190875 (3.4 ppm). $\nu_{max}$ (cm⁻¹): 3355 (N—H), 3082, 3065, 3024 (Ar C—H), 2959, 2931, 2872 (methyl and methylene C—H), 1598, 1494, 1450 (Ar C=C). m/e (CI) 254 (MH⁺, 100%).

1.5 (S)-α-(Diphenylmethyl)-α-isobutyl-methylamine 18

(S)-2-Amino-1,1-diphenyl-4-methylpentan-1-ol

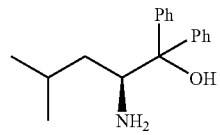

16

A 1 M solution of phenylmagnesium bromide (96.1 g, 0.53 mol) in THF was added dropwise at 0° C. to (S)-leucine methyl ester hydrochloride (19.3 g, 0.11 mol) and then stirred for 17 h at room temperature. The reaction mixture was cooled to 0° C., quenched with dropwise addition of saturated NH₄Cl and then diluted with AcOEt and water until partition occurred. Organic products were extracted into AcOEt (3×100 ml), dried over MgSO₄/K₂CO₃ and concentrated to obtain a crude product. The crude product was dissolved in diethyl ether (400 ml), treated with concentrated HCl until all of the amine was converted to its HCl salt. The amine-HCl salt was stirred overnight and then diluted with water until partition occurred. The non-basic organics were extracted into diethyl ether (5×100 ml) and then the aqueous layer was made basic with NaOH pellets. After stirring for 4 h, organic products were extracted into AcOEt (4×200 ml) and dried over MgSO$_4$/K$_2$CO$_3$. Concentration gave a crude product (13.7 g, 48%) as a pale yellow solid. This contaminated with the amino ester of the unreacted starting material, however was used directly for the next step without further purification. A small amount of the crude product (1.31 g) was purified over silica gel by means of dry-flash column chromatography, eluting first with CH$_2$Cl$_2$, then a mixture of AcOEt and petrol, increasing from 30% up to 55%. From this, a pure amino alcohol 16 (852 mg, 65%) was obtained as a white amorphous solid. m.p. 131–132° C. (lit 132–134° C.). $[\alpha]_D^{25}$=−101.0° (c, 5.38 in CHCl$_3$) (lit: −95.1° (c, 1.01 in CHCl$_3$)). $\delta_H$ 0.79 (6H, dd, J=7.20 and 7.80 Hz, CH$_3$), 0.86–1.80 (6H), 3.89 (1H, J=9.6 Hz, CH—NH$_2$), 7.00–7.70 (10H, m, Ar—H). $\delta_C$ 21.1, 23.8, 25.1, 39.2, 54.3, 78.9, 125.4, 125.6, 126.1, 126.4, 127.8, 128.2, 144.3, 147.0 (Ar). $\nu_{max}$ (cm$^{-1}$): 3337, 3268 (N—H and O—H), 3025 (Ar C—H), 2954, 2935, 2866 (methyl and methylene C—H), 1597, 1491, 1448 (Ar C=C). m/e 270 (MH$^+$, 5%), 252 (M—OH, 11%), 86 (100%).

(4S)-4-Isobutyl-5,5-diphenyl-2-oxazolidinone 17

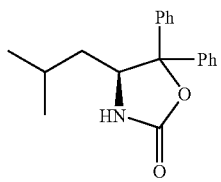

17

Trichloromethyl chloroformate (13.0 g, 65.8 mmol) was added to a mixture of (S)-2-amino-1,1-diphenyl-4-methyl-pentan-1-ol 16 (12.4 g of 65%, 29.9 mmol) and triethylamine (12.7 g, 125.5 mmol) in CH$_2$Cl$_2$ at 0° C. The reaction mixture was stirred for 15 h, allowing to warm to room temperature. The mixture was then washed with HCl (3×200 ml) and water (2×200 ml), and dried over MgSO$_4$. Concentration gave a crude product, which was washed with diethyl ether to afford the title compound 17 (7.9 g, 90%) as a white solid. m.p. 212–214° C. $[\alpha]_D^{25}$=−286.1° (c, 4.32 in CHCl$_3$). $\delta_H$ 0.85 (3H, d, J=6.6 Hz, CH$_3$), 0.91 (3H, d, J=6.6 Hz, CH$_3$), 0.96–1.08 (2H, m, CH$_2$), 1.53–1.73 (1H, m, CH—Me$_2$), 4.57 (1H, dd, J=10.5 and 3.60 Hz, CH—NH), 7.05 (1H, s, NH), 7.16–7.50 (10H, m, Ar—H). $\delta_C$ 20.8, 23.7, 24.9, 41.8, 58.8, 89.1, 125.9, 126.3, 127.6, 127.8, 128.1, 128.3, 139.3, 142.5 (Ar), 158.8 (C=O). $\nu_{max}$ (cm$^{-1}$): 3261, 3160 (N—H), 2955, 2869 (methyl and methylene C—H), 1752, 17235 (C=O), 1495, 1447 (Ar C=C), 1251 (C—O). m/e 313 (MNH$_4^+$, 12%), 296 (MH$^+$, 15%), 237 (100%).

(S)-α-(Diphenylmethyl)-α-isobutyl-methylamine 18

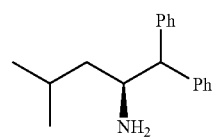

18

A suspension of (S)-4-isobutyl-5,5-diphenyl-2-oxazolidinone 17 (7.6 g, 25.6 mmol) in MeOH/AcOH and a 10% Pd (282 mg, 2.6 mmol) on activated carbon was shaken for 93 h under 4–5 atm pressure of hydrogen at room temperature. The catalyst was filtered off over Hyflo Super Cell and solvents were evaporated under reduced pressure. The resulting residue was treated with HCl until all of the amine was converted to its HCl salt, stirred overnight at room temperature and diluted with water until partitioned occurred. The non-basic organics were extracted into diethyl ether (2×100 ml) and then the aqueous layer was made basic with NaOH pellets. Organics were then extracted into CH$_2$Cl$_2$ (5×100 ml) and the combined extracts were dried over MgSO$_4$. Concentration gave the title product 18 (5.7 g, 87%) as a white amorphous solid. m.p. 46–48° C. $[\alpha]_D^{25}$=−31.6° (c, 4.12 CHCl$_3$). $\delta_H$ 0.86 (6H, dt, J=6.60 and 2.10 Hz, CH$_3$), 1.00–1.50 (4H, m and broad s, CH$_2$ and NH$_2$), 1.66–1.86 (1H, m, CH), 3.61 (2H, broad s, CH—NH$_2$ and CH—Ph$_2$), 7.10–7.40 (10H, m, Ar—H). $\delta_C$ 21.8 and 24.7 (CH$_3$), 25.5 (CH), 45.6 (CH$_2$), 52.4 (CH—NH$_2$), 61.6 (CH—Ph$_2$), 126.9, 127.1, 128.8, 129.0, 129.2, 129.4, 143.8, 144.0 (Ar). Accurate mass (CI): Found 254.190200; Calculated for (MH$^+$) C$_{18}$H$_{24}$N 254.190875 (2.7 ppm). $\nu_{max}$ (cm$^{-1}$): 3368 (N—H), 3057, 3027 (Ar C—H), 2951, 2932, 2909, 2867 (methyl and methylene C—H), 1595, 1494, 1450 (Ar C=C). m/e (CI) 254 (MH$^+$, 100%).

2. Chiral Amines wherein Z is F 2.1 (S)-α-(Fluorodiphenylmethyl)-α-[(R)-1-methylpropyl]-methylamine 19

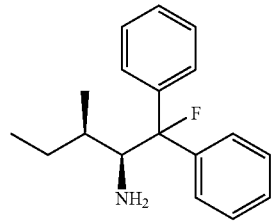

19

A solution of the oxazolidinone 14 (100 mg, 0.34 mmol) in CH$_2$Cl$_2$ (5 ml) was carefully added to 30% HF-pyridine (2 ml) (Olah's reagent) in a polythene bottle, and the contents were cooled to 0° C. The solution was allowed to reach ambient temperature over 24 hours and was then poured into ice-cooled 2N aqueous ammonia solution (50 ml). The organic layer was separated and the aqueous layer extracted into CH$_2$Cl$_2$ (3×30 ml). The combined organic layers were dried over MgSO$_4$ and were then filtered and the solvent removed under reduced pressure. Purification by flash-column over silica gel chromatography (eluting with EtOAc/PetEt 1:4) generated the fluorinated amine 19 as a white amorphous solid (23.1 mg, 25%). On the basis of recovered starting material the yield is corrected to 53%.

$[\alpha]_D$=−32.3° (MeOH, c=0.6), m.p.: 76.9° C.; $\delta_H$ (400 MHz; CDCl$_3$): 7.45–7.16 (10H, m, CH$_{ar}$.), 3.82 (1H, qd, J 25.60 and 6.40, CH—NH$_2$), 1.65 (2H, s, NH$_2$), 1.03 (3H, J 6.80, CH$_3$); $\delta_F$ (376 MHz; CDCl$_3$): −174.91 (d, J 24.46)

HRMS (CI, M+H$^+$) found 272.1814. C$_{18}$H$_{22}$NF requires 272.1815.

2.2 (S)-α-(Fluorodiphenylmethyl)-α-isobutyl-methylamine 20

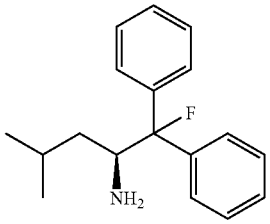

A solution of the oxazolidinone 16 (150 mg, 0.51 mmol) in CH$_2$Cl$_2$ (5 ml) was carefully added to 30% HF-pyridine (1.5 ml) (Olah's reagent) in a polythene bottle, and the contents were cooled to 0° C. The solution was allowed to reach ambient temperature over 24 hours and was then poured into ice-cooled 2N aqueous ammonia solution (50 ml). The organic layer was separated and the aqueous layer extracted into CH$_2$Cl$_2$ (3×30 ml). The combined organic layers were dried over MgSO$_4$ and were then filtered and the solvent removed under reduced pressure. Purification by flash-column over silica gel chromatography (eluting with EtOAc/CH$_2$Cl$_2$, 1:4) generated the fluorinated amine 14 as a white amorphous solid (61 mg, 44%). On the basis of recovered starting material the yield is corrected to 61%.

[α]$_D$=−48.78° (MeOH, c=1.2); m.p.: 84° C.; δ$_H$ (400 MHz; CDCl$_3$): 7.50–7.26 (10H, m, CH$_{ar}$), 3.72 (1H, ddd, J 26.0, 10.4 and 2.0, CH—NH$_2$), 1.85 (1H, m, CH(CH$_3$)$_2$), 1.51 (2H, s, NH$_2$), 1.35 (1H, m, CH$_A$H$_b$), 1.18 (1H, m, CH$_A$H$_b$), 0.87 (6H, t, J 6.4, 2CH$_3$); δ$_F$ (376 MHz: CDCl$_3$): −174.1 (d, J 30.12); m/z (EI): 251 (5%, M—HF), 208 (26, [M—HF]—CH(CH$_3$)$_2$), 194 (8, [M—HF]—CH$_2$CH (CH$_3$)$_2$); HRMS (CI, M+H$^+$) found 272.1812. C$_{18}$H$_{22}$NF requires 272.1815.

2.3 (S)-2-(Fluorodiphenylmethyl)-pyrrolidine 21

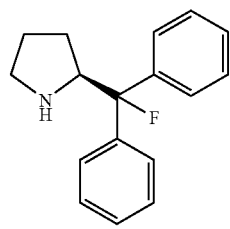

A solution of the oxazolidinone (200 mg, 0.7 mmol) in CH$_2$Cl$_2$ (5 ml) was carefully added to 30% HF-pyridine (2 ml) (Olah's reagent) in a polythene bottle, and the contents were cooled to 0° C. The solution was allowed to reach ambient temperature over 24 hours and was then poured into ice-cooled 2N aqueous ammonia solution (50 ml). The organic layer was separated and the aqueous layer extracted into CH$_2$Cl$_2$ (3×30 ml). The combined organic layers were dried over MgSO$_4$ and were then filtered and the solvent removed under reduced pressure. Purification by flash-column over silica gel chromatography (eluting with EtOAc/petrol, 6:4) generated the fluorinated amine 14 and a viscous oil (55.8 mg, 31%).

[α]$_D$=−8.08° (MeOH, c 7.4), δ$_H$ (400 MHz; CDCl$_3$): 7.47–7.16 (10H, m, CH$_{ar}$), 4.14 (1H, td, J 28.40 and 7.20, CH), 3.02–2.95 (1H, m, CH$_A$H$_B$—NH), 2.85–2.77 (1H, m, CH$_A$H$_B$—NH), 1.81–1.20 (2H, m, NH and 2CH$_2$); δ$_F$ (376 MHz; CDCl$_3$): −171.02 (d, J 27.47). m/z (CI): 256 (76%, M+1), 236 (100, [M—HF]+1); HRMS (CI, M+H$^+$) found 256.1499. C$_{17}$H$_{18}$NF requires 256.1502.

R. E. Gawley and P. Zhang, *J. Org. Chem.*, 1996, 61, 8103.
1. S. Itsuno, M. Nakano, K. Miyazaki, H. Masuda, K. Ito, A. Hirao and S. Nakahama, *J. Chem. Soc., Perkin Trans. 1*, 1985, 2039.
2. T. Akiba, O. Tamura, M. Hashimoto, Y. Kobayashi, T. Katoh, K. Nakatani, M. Kamada and S. Terashima, *Tetrahedron*, 1994, 50 (13), 3905.
3. S. Itsuno, M. Nakano, K. Miyazaki, K. Ito, A, Hirao, M. Owa and S. Nakahama, *J. Chem. Soc., Perkin Trans. 1*, 1985, 2615.
4. E. Weber, C. Reutel, C. Foces-Foces and A. L. Llamas-Saiz, *J. Phys. Org. Chem.*, 1995, 8, 159.
5. F. Dammast and H-U. Reiβig, *Chem. Ber.*, 1993, 126, 2449.

What is claimed is:

1. An enantiomerically pure compound of the formula I wherein X is N and n is 1

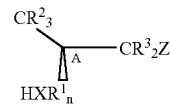

wherein
A is an enantiomerically pure centre CH; Z is hydrogen or fluoro;
and wherein
R$^1$ is selected from hydrogen or from straight chain or branched, saturated or unsaturated C$_{1-8}$ hydrocarbon optionally substituted by one or more hydroxy, halo, aryl, cyclo C$_{1-8}$ alkyl;
each R$^3$ is independently selected from halo, except when Z=F, then R$^3$≠F; or straight or branched chain, saturated or unsaturated C$_{1-4}$ alkyl, alkenyl, alkynyl or aryl; each optionally substituted by hydroxy, halo, saturated or unsaturated C$_{1-4}$ alkyl, alkenyl or alkynyl, aryl, cyclo C$_{1-6}$ alkyl, carbonyl, carboxyl, amino, amido;
each R$^2$ is independently selected from hydrogen, straight chain or branched, saturated or unsaturated C$_{1-8}$ alkyl, alkenyl, or alkynyl; each optionally substituted by hydroxy, aryl, cyclo C$_{1-6}$ alkyl, carbonyl, carboxyl, amino, amido, or aryl; and
one R$^1$ and one of R$^2$ together may form an alkylene group as part of a heterocyclic ring;
with the proviso that when two of R$^2$ are hydrogen, CR$^3{}_2$ is CPh$_2$ and Z is hydrogen, R$^1$ and the other R$^2$ do not form together a five membered heterocyclic (pyrrolidone) ring; and wherein CR$^3{}_2$Z does not comprise a chiral center.

2. The compound as claimed in claim 1, wherein R$^3$ is selected from a group consisting of ethenyl, ethynyl and optionally substituted phenyl.

3. The compound as claimed in claim 1, wherein at least one R$^3$ is aryl.

4. The compound as claimed in claim 1, wherein R$^2$ is selected from a group consisting of optionally hydroxyl, halo or alkoxy substituted branched and straight chain C$_{1-6}$ alkyl, including methyl, ethyl, i-propyl, i-butyl, t-butyl; and aryl.

5. The compound as claimed in claim 1, wherein X is nitrogen, n is 1 and R$^1$ is H.

6. The compound as claimed in claim 1, wherein each $R^2$ is independently selected from hydrogen or aryl.
7. The compound as claimed in claim 1, wherein at least one $R^3$ is aryl.
8. The compound as claimed in claim 1, wherein $R^2$ is phenyl or benzyl.
9. The compound as claimed in claim 1, wherein $R^1$ is hydrogen, $CR^2{}_3$ is $CH_2Ph$, $CR^3{}_2$ is $CPh_2$ and Z is hydrogen as shown in formula III:
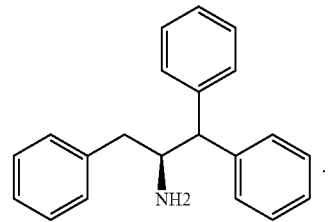
* * * * *